(12) United States Patent
Liu

(10) Patent No.: US 12,315,062 B2
(45) Date of Patent: *May 27, 2025

(54) METHOD AND SYSTEM FOR SIMULATING A VIRTUAL PERFORMANCE USING VIRTUAL CHARACTERS FOR CONTENT VIEWERS

(71) Applicant: HYTTO PTE. LTD, Singapore (SG)

(72) Inventor: Dan Liu, Guangdong (CN)

(73) Assignee: HYTTO PTE. LTD., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 18/921,099

(22) Filed: Oct. 21, 2024

(65) Prior Publication Data

US 2025/0045999 A1 Feb. 6, 2025

Related U.S. Application Data

(63) Continuation-in-part of application No. 18/387,822, filed on Nov. 7, 2023, now Pat. No. 12,154,206, and
(Continued)

(51) Int. Cl.
| | |
|---|---|
| G06T 13/40 | (2011.01) |
| G06F 3/01 | (2006.01) |
| G06T 7/20 | (2017.01) |
| G06T 13/80 | (2011.01) |
| H04N 21/234 | (2011.01) |

(52) U.S. Cl.
CPC ............ G06T 13/40 (2013.01); G06F 3/011 (2013.01); G06T 7/20 (2013.01); G06T 13/80 (2013.01); H04N 21/23418 (2013.01); G06T 2200/24 (2013.01)

(58) Field of Classification Search
CPC .......... G06T 13/40; G06T 7/20; G06T 13/80; G06T 2200/24; G06F 3/011; H04N 21/23418
See application file for complete search history.

(56) References Cited

U.S. PATENT DOCUMENTS

| | | |
|---|---|---|
| 6,368,268 B1 | 4/2002 | Sandvick et al. |
| 10,685,488 B1 | 6/2020 | Kumar |
| (Continued) | | |

OTHER PUBLICATIONS

Notice of Allowance dated Jul. 22, 2024, issued in parent U.S. Appl. No. 18/387,822.
(Continued)

*Primary Examiner* — Terrell M Robinson
(74) *Attorney, Agent, or Firm* — Holtz, Holtz & Volek PC

(57) ABSTRACT

Embodiments of the present disclosure provide methods and systems for broadcasting virtual performance. Motion data related to a performer is received from one or more sensors during a physical performance of the performer. The motion data is processed to animate movements of at least one virtual character. A virtual performance corresponding to the physical performance is generated based, at least in part, on the animated movements of the virtual character. The virtual performance is broadcasted to a viewer device for performing a playback of the virtual performance. The virtual performance simulates an experience of viewing the physical performance for the viewer.

20 Claims, 7 Drawing Sheets

Related U.S. Application Data a continuation-in-part of application No. 17/812,602, filed on Jul. 14, 2022, and a continuation-in-part of application No. 17/748,294, filed on May 19, 2022, said application No. 17/812,602 is a continuation-in-part of application No. 17/717,917, filed on Apr. 11, 2022, now Pat. No. 11,938,078, said application No. 18/387,822 is a continuation of application No. 17/529,255, filed on Nov. 17, 2021, now Pat. No. 11,854,137, said application No. 17/812,602 is a continuation-in-part of application No. 17/520,889, filed on Nov. 8, 2021, said application No. 17/748,294 is a continuation-in-part of application No. 17/088,476, filed on Nov. 3, 2020, now Pat. No. 11,503,384, said application No. 17/812,602 is a continuation-in-part of application No. 16/835,808, filed on Mar. 31, 2020, now Pat. No. 11,452,669, said application No. 17/088,476 is a continuation-in-part of application No. 16/538,825, filed on Aug. 13, 2019, now Pat. No. 10,945,914, said application No. 17/717,917 is a continuation of application No. 16/352,876, filed on Mar. 14, 2019, now Pat. No. 11,311,453.

(60) Provisional application No. 63/140,404, filed on Jan. 22, 2021, provisional application No. 62/830,195, filed on Apr. 5, 2019.

(56) References Cited

U.S. PATENT DOCUMENTS

| | | | |
|---|---|---|---|
| 2006/0079732 A1 | 4/2006 | Blumenthal | |
| 2007/0055096 A1 | 3/2007 | Berry et al. | |
| 2008/0079752 A1 | 4/2008 | Gates et al. | |
| 2011/0187640 A1 | 8/2011 | Jacobsen et al. | |
| 2011/0242134 A1* | 10/2011 | Miller | G06F 3/017 345/633 |
| 2012/0258802 A1 | 10/2012 | Weston et al. | |
| 2012/0326976 A1 | 12/2012 | Markovic et al. | |
| 2014/0003762 A1 | 1/2014 | Macnamara | |
| 2014/0031086 A1 | 1/2014 | Yoo | |
| 2015/0336016 A1* | 11/2015 | Chaturvedi | A63H 30/04 446/484 |
| 2015/0375115 A1 | 12/2015 | Bunting et al. | |
| 2016/0041391 A1* | 2/2016 | Van Curen | A63F 13/211 345/633 |
| 2016/0224103 A1* | 8/2016 | Kochi | A63F 13/65 |
| 2020/0388066 A1 | 12/2020 | Miller et al. | |

OTHER PUBLICATIONS

Office Action (Non-Final Rejection) dated Jun. 4, 2024, issued in parent U.S. Appl. No. 18/387,822.

* cited by examiner

METHOD AND SYSTEM FOR SIMULATING A VIRTUAL PERFORMANCE USING VIRTUAL CHARACTERS FOR CONTENT VIEWERS

CROSS REFERENCE TO RELATED APPLICATIONS

This application is a continuation in part application of U.S. application Ser. No. 18/387,822, filed Nov. 7, 2023, which is a continuation application of U.S. application Ser. No. 17/529,255, filed Nov. 17, 2021, and issued as U.S. Pat. No. 11,854,137 on Dec. 26, 2023, and claims the benefit of Provisional Patent Application Ser. No. 63/140,404, filed Jan. 22, 2021. This application is also a continuation in part application of U.S. application Ser. No. 17/812,602, filed Jul. 14, 2022, which is a continuation in part of U.S. application Ser. No. 17/520,889, filed Nov. 8, 2021, and is a continuation in part of U.S. application Ser. No. 17/717,917, filed Apr. 11, 2022, and issued as U.S. Pat. No. 11,938,078 on Mar. 26, 2024. U.S. application Ser. No. 17/717,917 is a continuation of U.S. application Ser. No. 16/352,876, filed Mar. 14, 2019, and issued as U.S. Pat. No. 11,311,453 on Apr. 26, 2022. U.S. application Ser. No. 17/812,602 is also a continuation in part of U.S. application Ser. No. 16/835,808 filed Mar. 31, 2020, and issued as U.S. Pat. No. 11,452,669 on Sep. 27, 2022. U.S. application Ser. No. 16/835,808 claims the benefit of Provisional patent Application Ser. No. 62/830,195 filed Apr. 5, 2019. This application is also a continuation in part application of U.S. application Ser. No. 17/748,294, filed May 19, 2022, which is a continuation in part application of U.S. application Ser. No. 17/088,476, filed Nov. 3, 2020, and issued as U.S. Pat. No. 11,503,384, on Nov. 15, 2022, which is a continuation in part application of U.S. application Ser. No. 16/538,825, filed Aug. 13, 2019, and issued as U.S. Pat. No. 10,945,914, on Mar. 16, 2021. Each of the above applications is hereby incorporated by reference in its entirety.

TECHNICAL FIELD

The present technology generally relates to simulation systems employing motion capture and, more particularly, to a system and method for simulating a virtual performance using virtual characters for content viewers using real-time rendering effect.

BACKGROUND

In recent times, digital content streaming, especially livestreaming, has been hugely popular among viewers of digital content. Most often, when viewers cannot flock to venues for viewing live performance (also referred to as 'physical performance'), livestreaming of the physical performance allow artists to broadcast their live performances to audiences. Moreover, such livestreaming content provides an exciting opportunity for the performers to engage with their audiences in real-time.

Conventionally, multiple cameras surrounding a volume of space capture visual information of the physical performance. More specifically, the cameras capture visual information representative of the performer's movement in the real-world and processing systems may relay the visual information to the audiences in real-time. However, the internet has become an increasingly dangerous place for sexual predators and stalkers who may use publicly displayed data (i.e., livestreaming content) to target vulnerable performers. For example, specific online activities such as, interacting online with unknown people, posting video content and personal information may provide a platform for such predators to befriend potential targets and exploit them. Therefore, some performers may choose not to leave subtle clues about themselves and remain anonymous during their performance to protect their identity from online predators and internet identity thieves. Moreover, viewers like to be in control of the performance of the performer, for example, the dance moves of the performer or the song for which the performer dances. In general, exercising such control over the performer enhances the reality of an unreal virtual environment for the viewer and enhances the viewer's engagement in the action.

In light of the above discussion, there appears a need to facilitate increased engagement for viewers with the virtual character while overcoming the drawbacks of current mapping techniques from the physical performance to the virtual performance. Further, it would be advantageous to simulate the experience of attending the live performance for the viewer of the virtual performance to enhance the overall quality of experience provided to the viewer.

SUMMARY

Various embodiments of the present disclosure provide methods and systems for simulating a virtual performance using virtual characters for content viewers.

In an embodiment, a computer-implemented method for broadcasting virtual performance is disclosed. The computer-implemented method performed by a system includes receiving motion data related to a performer from a plurality of sensors during a physical performance of the performer. The method includes processing the motion data to animate movements of at least one virtual character. The method also includes generating a virtual performance corresponding to the physical performance based, at least in part, on the animated movements of the at least one virtual character. The method includes broadcasting the virtual performance to a viewer device for performing a playback of the virtual performance. The virtual performance simulates an experience of viewing the physical performance for the viewer.

In another embodiment, a system is disclosed. The system includes a memory storing executable instructions and a processor operatively coupled with the memory. The processor is configured to execute the executable instructions to cause the system to at least receive motion data related to a performer from a plurality of sensors during a physical performance of the performer. The system is further caused to process the motion data to animate movements of at least one virtual character. The system is further caused to generate a virtual performance corresponding to the physical performance based, at least in part, on the animated movements of the at least one virtual character. The system is further caused to broadcast the virtual performance to a viewer device for performing a playback of the virtual performance, wherein the virtual performance simulates an experience of viewing the physical performance for the viewer.

In yet another embodiment, a computer-implemented method for broadcasting virtual performance is disclosed. The computer-implemented method performed by a system includes receiving motion data related to a performer from a plurality of sensors during a physical performance of the performer. The plurality of sensors corresponds to one or more of: a motion sensor configured on a body of the performer, and an image sensor positioned at an enclosed space to capture the motion data of the performer. The method includes processing the motion data to animate movements of at least one virtual character. The motion data related to the performer is mapped to a bone position axial data of the at least one virtual character for animating the movements of the at least one virtual character. The method also includes adding one or more special effects to enhance the animated movements of the virtual character. The method further includes generating a virtual performance corresponding to the physical performance based, at least in part, on the animated movements of the at least one virtual character and the one or more special effects. The method includes broadcasting the virtual performance to a viewer device for performing a playback of the virtual performance, wherein the virtual performance simulates an experience of viewing the physical performance for the viewer.

BRIEF DESCRIPTION OF THE FIGURES

The following detailed description of illustrative embodiments is better understood when read in conjunction with the appended drawings. For the purpose of illustrating the present disclosure, exemplary constructions of the disclosure are shown in the drawings. However, the present disclosure is not limited to a specific device or a tool and instrumentalities disclosed herein. Moreover, those in the art will understand that the drawings are not to scale. Wherever possible, like elements have been indicated by identical numbers.

Figure 1:
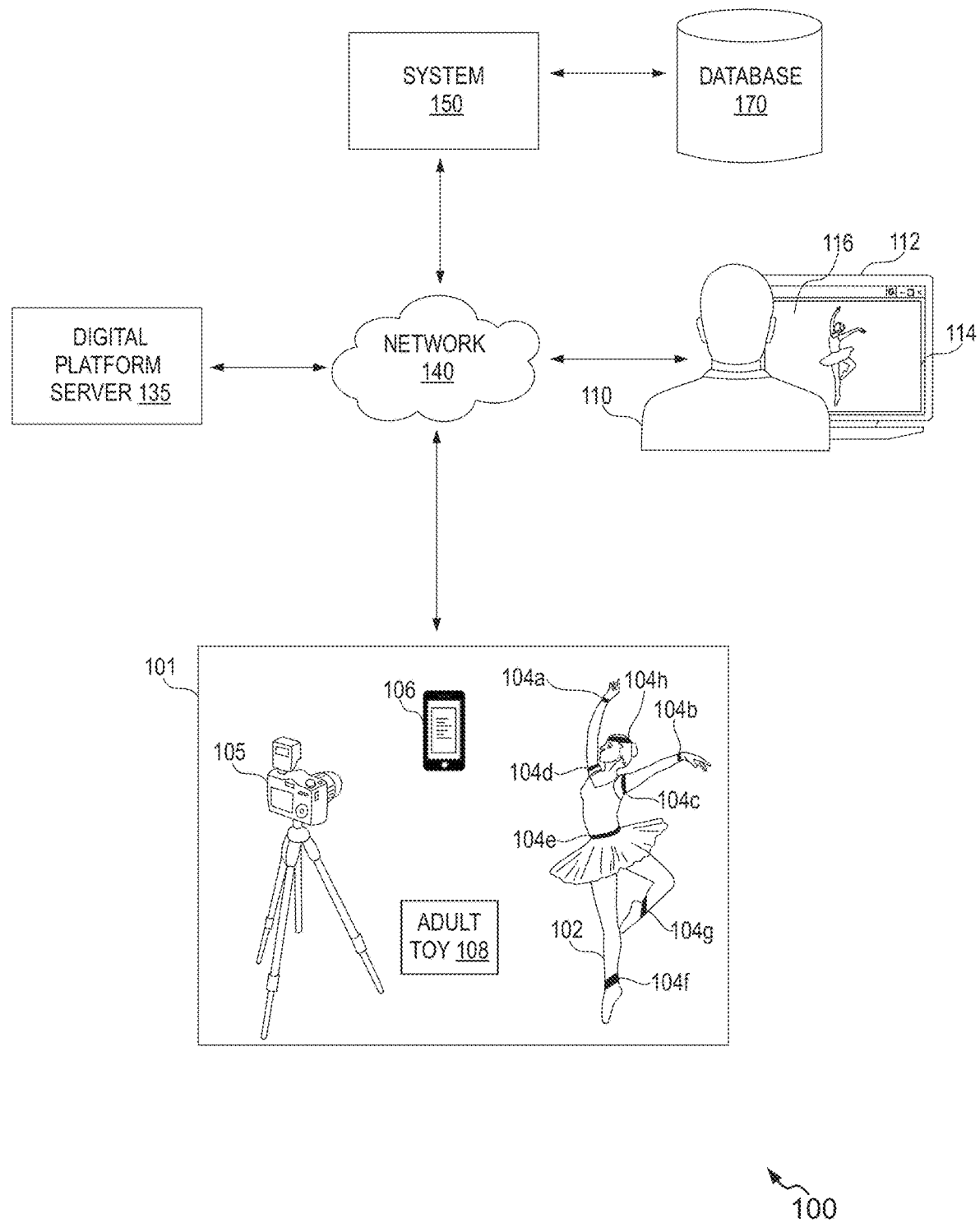
FIG. 1 is an example representation of an environment related to at least some example embodiments of the invention.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

The term 'physical performance' as used herein refers to an activity or presentation done by one or more people before audience present at an event venue. For example, an act of staging or presenting a play, theatre, music, dance, role-play and the like before audiences is referred to as physical performance. In general, people performing an act/event live before audiences present at the event venue is referred to as physical performance.

On the contrary, the term 'virtual performance' refers to an online media broadcast of media content corresponding to the physical performance in real-time to electronic devices associated with audiences. In general, livestreaming of media content to electronic devices of content viewers is referred to as virtual performance. In one illustrative example, the real-time broadcast of a live concert to a smartphone or television of a viewer is referred to as virtual performance. In a virtual performance, the audience get to watch live performances from the comfort of their house. Accordingly, a person who watches media content broadcasted in real-time is referred to as 'content viewer' or 'viewer' and a person who acts, sings or performs before audiences to entertain them is referred to as 'performer' or 'model'.

Various example embodiments of simulating and broadcasting a virtual performance using virtual characters are further explained in detail with reference to FIGS. 1 to 8.

FIG. 1 is an example representation of an environment 100 related to at least some example embodiments of the invention. Although the environment 100 is presented in one arrangement, other arrangements are also possible where the parts of the environment 100 are arranged or interconnected differently. The environment 100 exemplarily depicts a performer 102 staging an act, for example, dancing at a venue 101. In at least one example embodiment, a plurality of sensors is utilized to capture movements of the performer 102. In general, motion data related to movements of the performer are captured by the plurality of sensors.

In one embodiment, one or more of the plurality of sensors correspond to motion sensors. Accordingly, the performer 102 wears motion sensors 104a, 104b, 104c, 104d, 104c, 104f, 104g at different parts of his/her body. More specifically, the motion sensors 104a, 104b, 104c, 104d, 104c, 104f, 104g are enclosed in a material, for example a piece of cloth and wrapped around specific parts of the performer's body, for instance, hands (motion sensors 104a and 104b), shoulders (motion sensors 104c and 104d), waist (motion sensor 104c), feet (motion sensors 104f and 104g) and head (motion sensor 104h). It shall be noted that the motion sensors in this illustration are shown for exemplary purposes only and more or few number of motion sensors may be positioned at some other locations of the body of the performer 102 that are different from the locations depicted in the FIG. 1 to capture appropriate movements of the performer 102. In at least one example embodiment, the motion sensors 104a, 104b, 104c, 104d, 104c, 104f, 104g are inertial sensors. Typically, the motion sensors 104a, 104b, 104c, 104d, 104c, 104f, 104g are designed to detect and capture the movements of the performer 102 from the different parts of the body. Examples of the movements include, but are not limited to, jumping, shaking head, waving hand, rolling, crawling, dancing, and the like. In another embodiment, one or more of the plurality of sensors correspond to sensors coupled to the adult toy used by the performer 102.

In another embodiment, one or more sensors of the plurality of sensors correspond to image sensors that capture movement of the performer. As shown in FIG. 1, an image sensor (i.e., camera 105) may be installed in an enclosed space such as, the venue 101 for capturing motion data related to the performer 102. In general, the image sensor 105 captures a plurality of image frames related to the performance of the performer 102 and the plurality of image frames are processed to determine the motion data related to the movements of the performer 102. It shall be noted that the image sensor 105 in this illustration is shown for exemplary purposes only and a greater number of image sensors may be positioned at different locations of the venue 101 to capture appropriate motion data related to the performer 102.

In an embodiment, the image sensor 105 has the capability to provide the motion data in situations when motion data from the sensors 104a, 104b, 104c, 104d, 104e, 104f, and 104g are not received and thus acts as a fallback. In one illustrative example, if the performer 102 is performing a movement that may not be captured by any of the motion sensors 104a, 104b, 104c, 104d, 104c, 104f, and 104g, for example, a facial expression depicting a pleasure on performing specific movements, the facial expressions are captured by the image sensor 105. In general, the image sensor 105 and the motion sensors 104a, 104b, 104c, 104d, 104c, 104f, and 104g complement each other to track movements of the performer 102 for determining the motion data. Therefore, the present disclosure has the advantage of including a backup option or a fallback mode to track movements of the performer 102.

Further, the performer 102 may be associated with an electronic device 106 (also referred to herein as 'performer device 106') and an adult toy 108. Some examples of the performer device 106 include, but not limited to, laptops, smartphones, desktops, tablets, workstation terminals, an Ultra-Mobile personal computer (UMPC), a phablet computer, a handheld personal computer, a web-enabled wearable device and the like. The performer 102 may be configured to perform using the adult toy 108 and the performer device 106 may be used to operate and control the adult toy 108. Examples of the adult toy 108 may include, but are not limited to, a dildo, a vibrator, or any adult entertainment apparatus. The adult toy 108 may be connected wirelessly with the performer device 106. Some examples for enabling wireless connectivity between the adult toy 108 and the performer device 106 may include, but not limited to, near field communication (NFC), wireless fidelity (Wi-Fi), Bluetooth and the like. It shall be noted that although the performer 102 is shown to be associated with one adult toy 108, the performer 102 may utilize more than one adult toy during the physical performance for experiencing physical stimulus.

The environment 100 includes a digital platform server 135 configured to broadcast virtual performances over the communication network 140 to electronic devices of viewers, such as, a viewer 110. The digital platform server 135 may be a content provider, for example, a livestreaming service provider who facilitates broadcasting of virtual performances. In this example representation, the viewer 110 is depicted as accessing a web interface 114 using a viewer device 112. In one embodiment, the viewer 110 may have downloaded a software application corresponding to the content provider from the digital platform server 135 on the viewer device 112 and the web interface 114 may be facilitated by the digital platform server 135. It is understood that the viewer device 112 may be in operative communication with a communication network 140 for viewing virtual performances of performers. The viewer device 112 is depicted to be a desktop computer for illustration purposes. However, it must be noted that the viewer 110 may use one or more electronic devices, such as a smartphone, a laptop, a desktop, a personal computer or any spatial computing device to view the virtual performance broadcasted by the digital platform server 135.

Viewers, such as the viewer 110, may access the web interface 114 to view interactive virtual performances such as, concerts, role-plays, theatre, dance, music, and the like. It shall be noted that the web interface 114 may correspond to a website or application broadcasting virtual performances of one or more performers such as, the performer 102 to live audiences, for example, the viewer 110. Further, it is noted that the viewer 110 may use the viewer device 112, such as but not limited to, a smartphone, a tablet computer, a mobile phone, a laptop computer, a personal digital assistant, a web-enabled wearable device and the like, for accessing the web interface 114.

The viewer device 112 may include necessary applications, such as for example, a Web browser application to enable the viewer 112 to access the web interface 114. The web interface 114 may broadcast performances of the performer 102 in real-time via a communication network 140. Some examples of the communication network 140 may include wired networks, wireless networks or a combination thereof. Examples of wired networks may include the Ethernet, local area networks (LANs), fiber-optic cable networks and the like. Examples of wireless networks may include cellular networks like GSM/3G/4G/CDMA based networks, wireless LANs, Bluetooth or Zigbee networks and the like. An example of a combination of wired and wireless networks may include the Internet.

The environment 100 also includes a system 150 configured to perform one or more of the operations described herein. In an embodiment, the system 150 may be configured to simulate a virtual performance corresponding to the physical performance of the performer 102. More specifically, the system 150 processes the movements of the performer 102 captured by the motion sensors 104a, 104b, 104c, 104d, 104, 104f, 104g to animate a virtual character 116. In at least one example embodiment, the virtual performance is broadcasted to audiences such as, the viewer 110.

The term 'virtual character' as used herein refers to a computer-generated model that is configured to mimic movements of the performer 102. More specifically, the virtual character 116 is an avatar or a graphical image that depicts an animated version of the performer 102. In general, the movements of the virtual character 116 are adapted based on movements of the performer 102. More specifically, movements of the performer 102 are tracked from the motion sensors 104a, 104b, 104c, 104d, 104e, 104f, 104g are used to animate movements of the virtual character 116. The movements of the virtual character 116 simulate the physical performance of the performer 102 for the viewer 110 on the viewer device 112.

The environment 100 further includes one or more databases, such as a database 170. In an embodiment, the database 170 may be a separate entity (or an external database) that is in communication with the system 150 via the network 140. The database 170 may be configured to store information such as special effects (e.g., audio data, background animation, etc.), control patterns for adult toy, virtual character features, animation effects, and the like. In at least one example embodiment, the system 150 may use the information stored in the database 170 to simulate and enhance the virtual performance being broadcasted to the viewer 110.

In some example embodiments, the system 150 displays rewards on the web interface 114 of the viewer device 112. The rewards may correspond to a monetary gain for the performer 102 if he/she performs an action associated with the reward. The viewer 110 may select a reward for the performer and accordingly the system 150 may send a request to the performer 102 for performing a specific action/movement. Such specific actions may require the performer 102 to perform with one or more adult toys, such as, the adult toy 108. To that effect, the system 150 is configured to identify a control pattern to operate the adult toy 108. The control pattern is sent to the viewer device 112 that controls operation of the adult toy 108 to provide physical stimulus for the performer 102. Such physical stimulus may alter movements of the performer 102 that are captured as motion data and processed further to adapt movements of the virtual character 116.

The system 150 is a separate part of the environment 100, and may operate apart from (but still in communication with, for example, via the network 140) other external servers, for example, the digital platform server 135 or databases to access data to perform the various operations described herein. However, in other embodiments, the system 150 may actually be incorporated, in whole or in part, into one or more parts of the environment 100, for example, the digital platform server 135. In addition, the system 150 should be understood to be embodied in at least one computing device in communication with the network 140, which may be specifically configured, via executable instructions, to perform as described herein, and/or embodied in at least one non-transitory computer readable media.

The number and arrangement of systems, devices, and/or networks shown in FIG. 1 are provided as an example. There may be additional systems, devices, and/or networks; fewer systems, devices, and/or networks; different systems, devices, and/or networks, and/or differently arranged systems, devices, and/or networks than those shown in FIG. 1.

Furthermore, two or more systems or devices shown in FIG. 1 may be implemented within a single system or device, and a single system or device shown in FIG. 1 may be implemented as multiple, distributed systems or devices. Additionally, or alternatively, a set of systems (e.g., one or more systems) or a set of devices (e.g., one or more devices) of the environment 100 may perform one or more functions described as being performed by another set of systems or another set of devices of the environment 100. The system 150 is explained in further detail with reference to FIG. 2.

Figure 2:
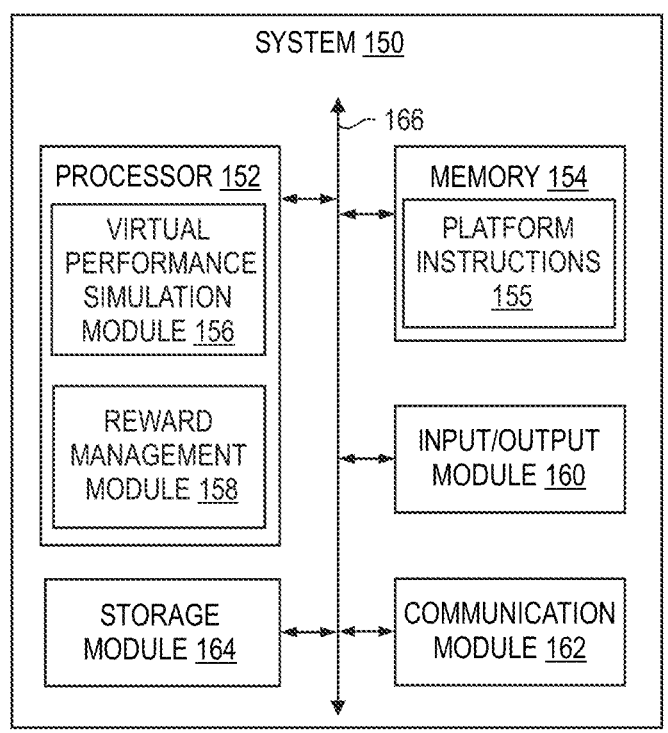
FIG. 2 is a block diagram of a system configured to broadcast a virtual performance for content viewers, in accordance with an embodiment of the invention.

FIG. 2 is a block diagram of the system 150 configured to broadcast a virtual performance for viewers, in accordance with an embodiment of the invention. The system 150 may be implemented in a server accessible over the communication network 140 (shown in FIG. 1). For example, the system 150 may be implemented in one or more computing devices as part of a server entity and may be in operative communication with the digital platform server 135 (shown in FIG. 1). Alternatively, in at least some embodiments, the system 150 may be implemented within the digital platform server 135.

The system 150 includes a processor 152 and a memory 154. It is noted that although the system 150 is depicted to include only one processor, the system 150 may include a greater number of processors therein. In an embodiment, the memory 154 is capable of storing machine executable instructions, referred to herein as platform instructions 155. Further, the processor 152 is capable of executing the platform instructions 155. In an embodiment, the processor 152 may be embodied as a multi-core processor, a single core processor, or a combination of one or more multi-core processors and one or more single core processors. For example, the processor 152 may be embodied as one or more of various processing devices, such as a coprocessor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like. In an embodiment, the processor 152 may be configured to execute hard-coded functionality. In an embodiment, the processor 152 is embodied as an executor of software instructions, wherein the instructions may specifically configure the processor 152 to perform the algorithms and/or operations described herein when the instructions are executed.

The processor 152 is depicted to include a virtual performance simulation module 156 and a reward management module 158. The virtual performance simulation module 156 and the reward management module 158 may be implemented as hardware, software, firmware or combinations thereof. The operation of the various modules of the processor 152 are explained in further detail later.

The memory 154 may be embodied as one or more volatile memory devices, one or more non-volatile memory devices, and/or a combination of one or more volatile memory devices and non-volatile memory devices. For example, the memory 154 may be embodied as semiconductor memories (such as mask ROM, PROM (programmable ROM), EPROM (erasable PROM), flash memory, RAM (random access memory), etc.), magnetic storage devices (such as hard disk drives, floppy disks, magnetic tapes, etc.), optical magnetic storage devices (e.g., magneto-optical disks), CD-ROM (compact disc read only memory), CD-R (compact disc recordable), CD-R/W (compact disc rewritable), DVD (Digital Versatile Disc) and BD (BLU-RAY® Disc).

In at least some embodiments, the memory 154 stores logic and/or instructions, which may be used by modules of the processor 152, such as the virtual performance simulation module 156, and the reward management module 158. For example, the memory 154 includes instructions for: (1) analyzing the motion data received from the image sensors and the motion sensors; (2) processing the motion data received in relation to a physical performance of a performer such as, the performer 102 from the plurality of sensors, (3) animating movements of a virtual character corresponding to movements of the performer 102, (4) simulating a virtual performance with the virtual character, (5) enhancing the virtual performance with special effects based on the animated movements, and (6) broadcasting the virtual performance to content viewers such as, the viewer 110 to stimulate an enhanced experience of the physical performance.

The system 150 further includes an input/output module 160 (hereinafter referred to as an 'I/O module 160') and at least one communication module such as a communication module 162. In an embodiment, the I/O module 160 may include mechanisms configured to receive inputs from and provide outputs to the operator(s) of the system 150. To that effect, the I/O module 160 may include at least one input interface and/or at least one output interface. Examples of the input interface may include, but are not limited to, a keyboard, a mouse, a joystick, a keypad, a touch screen, soft keys, a microphone, and the like. Examples of the output interface may include, but are not limited to, a display such as a light emitting diode display, a thin-film transistor (TFT) display, a liquid crystal display, an active-matrix organic light-emitting diode (AMOLED) display, a microphone, a speaker, a ringer, a vibrator, and the like. In an example embodiment, the processor 152 may include I/O circuitry configured to control at least some functions of one or more elements of the I/O module 160, such as, for example, a speaker, a microphone, a display, and/or the like. The processor 152 and/or the I/O circuitry may be configured to control one or more functions of the one or more elements of the I/O module 160 through computer program instructions, for example, software and/or firmware, stored on a memory, for example, the memory 154, and/or the like, accessible to the modules of the processor 152.

The communication module 162 may include communication circuitry such as for example, a transceiver circuitry including antenna and other communication media interfaces to connect to a communication network, such as the communication network 140 shown in FIG. 1. The communication circuitry may, in at least some example embodiments enable reception of: (1) motion data from motion sensors configured on body of the performer 102 (shown in FIG. 1), (2) motion data from the image sensors positioned in an enclosed space, for example, a concert hall/room where the performer 102 is staging an act, (3) viewer input on a reward corresponding to an action to be performed by the performer from the viewer device associated with a viewer, and (4) performer inputs indicating reward corresponding to an action from the performer device. The communication circuitry may further be configured to enable transmission of virtual performance directly to the viewer devices associated with content viewers (e.g., the viewer 110).

The system 150 is further depicted to include a storage module 164. The storage module 164 is any computer-operated hardware suitable for storing and/or retrieving data.

Figure 3:
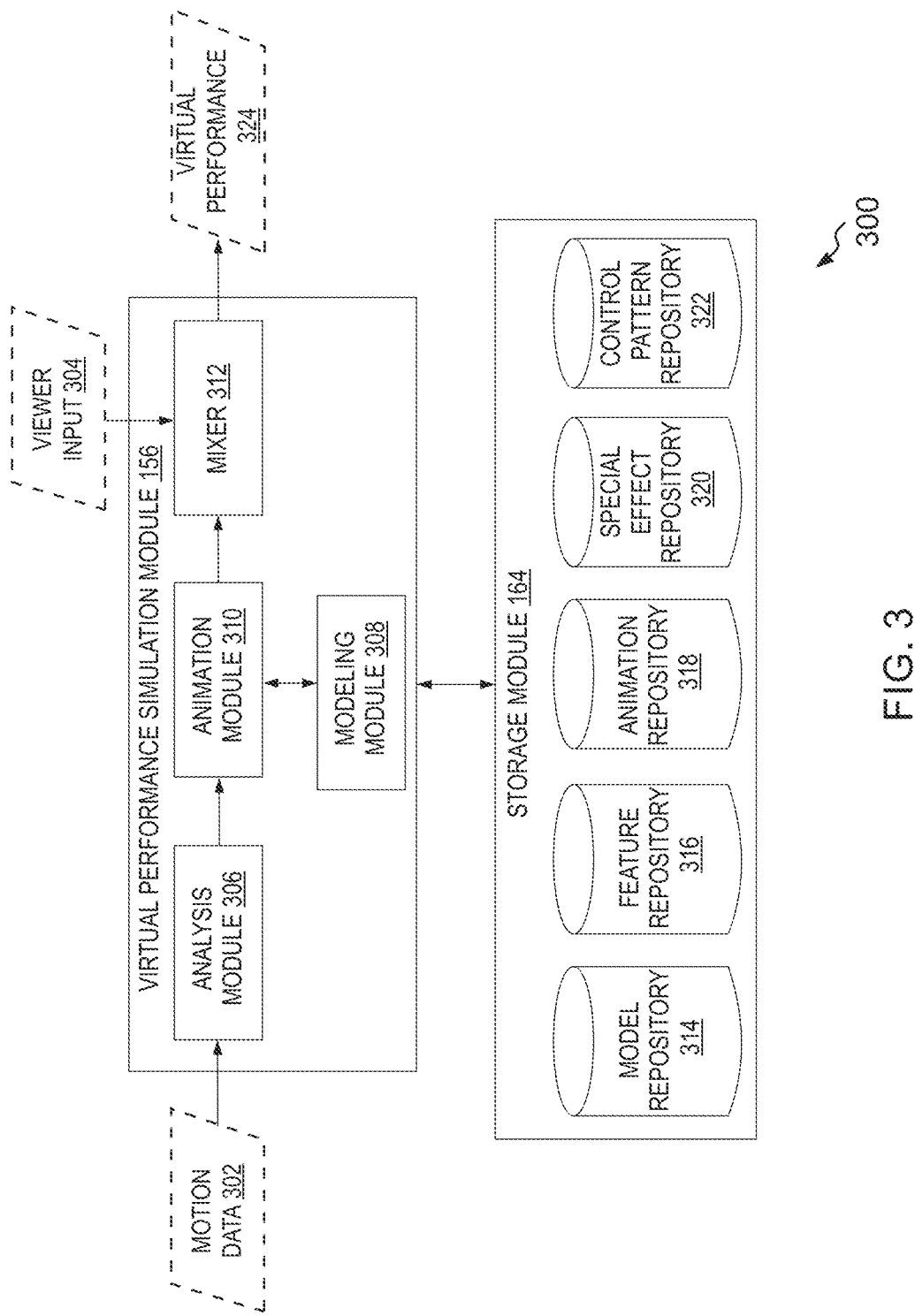
FIG. 3 is a block diagram of the virtual performance simulation module for illustrating a processing of motion data to generate a virtual performance, in accordance with an embodiment of the invention.

In one embodiment, the storage module 164 includes a model repository, a feature repository, an animation repository, a special effect repository and a control pattern repository (shown in FIG. 3). The model repository is configured to store a plurality of performer profiles associated with performers. Each performer profile may be associated with at least one virtual character. Therefore, the model repository stores a plurality of virtual characters corresponding to a plurality of performers.

The feature repository is configured to store a large variety of customization options for features associated with a virtual character. Such customization options for the features may be utilized by the performer to modify a specific feature, for example, change hair color from black to brown. In at least one example embodiment, the features may correspond to hair style, skin tone, eye color, body structure, clothes, and accessories. In one illustrative example, the feature repository may include customization options such as, pale ivory, yellow beige, warm beige, honey beige, golden brown, almond beige, olive brown, deep brown, golden bronze warm ivory, rose beige for modifying skin tone of the virtual character. In another illustrative example, accessories such as, ornaments, trinkets or props may be added to the virtual character to enrich appearance of the virtual character. The special effect repository includes a variety of audio clips, background effects, mechanized props and the like that may be used to enhance the virtual performance. For example, the special effect repository may include an audio clip that plays back sensual sounds and/or songs based on movements of the performer. As such, the special effect repository includes sounds related to different movements or actions in live performances related to individual or group live performances (e.g., theatre, music, dance, radio, etc.), entertainment shows, etc. that express happiness, joy or elation, pleasure or any other human reaction on experiencing physical stimulus or excitement. Similarly, mechanized props such as, balls, chair, or anything that may be used by the performer and background effects that enrich the virtual performance may be stored in the special effect repository.

The animation repository includes fragments of animations or human movements which can be accessed, analyzed and utilized to model the movements of the virtual character. A plurality of control patterns configured to operate a variety of adult toys for providing various physical stimulation are stored in the control pattern repository. More specifically, each control pattern is stored along with a corresponding reward information in the control pattern repository.

The storage module 164 may include multiple storage units such as hard drives and/or solid-state drives in a redundant array of inexpensive disks (RAID) configuration. In some embodiments, the storage module 164 may include a storage area network (SAN) and/or a network attached storage (NAS) system. In one embodiment, the storage module 164 may correspond to a distributed storage system, wherein individual databases are configured to store custom information, such as viewer inputs, viewer interaction data logs for various virtual performances.

In some embodiments, the processor 152 and/or other components of the processor 152 may access the storage module 164 using a storage interface (not shown in FIG. 2). The storage interface may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing the processor 152 and/or the modules of the processor 152 with access to the storage module 164.

The various components of the system 150, such as the processor 152, the memory 154, the I/O module 160, the communication module 162 and the storage module 164 are configured to communicate with each other via or through a centralized circuit system 166. The centralized circuit system 166 may be various devices configured to, among other things, provide or enable communication between the components of the system 150. In certain embodiments, the centralized circuit system 166 may be a central printed circuit board (PCB) such as a motherboard, a main board, a system board, or a logic board. The centralized circuit system 166 may also, or alternatively, include other printed circuit assemblies (PCAs) or communication channel media.

In at least one example embodiment, the communication module 162 is configured to receive motion data corresponding to movements of the performer in real-time from the plurality of sensors. For example, the communication module 162 may receive motion data corresponding to a live dance performance conducted at an event venue from the motion sensors (e.g., the motion sensors 104a, 104b, 104c, 104d, 104e, 104f, and 104g) and/or the image sensors (e.g., the image sensor 105). The motion data received from the motion sensors may include information corresponding to acceleration, inclination and vibration of the motion sensors configured on the body of the performer. Alternatively, the plurality of image frames captured by the image sensor may be processed using image processing techniques such as, motion estimation techniques to determine the motion data. The communication module 162 may be configured to collate the motion data received from the sensors (i.e., image sensors and/or motion sensors) and forward the motion data to the processor 152. The processing of the motion data by the processor 152 to simulate a virtual performance with a virtual character will be explained in further detail later.

In addition to receiving the motion data corresponding to the performer, the communication module 164 may also receive viewer input on at least one reward. The reward corresponds to an action to be performed by the performer. In at least some example embodiments, the digital platform server (for example, the digital platform server 135 shown in FIG. 1) may facilitate a plurality of selectable options on the web interface for the viewer. The plurality of selectable options corresponds to rewards that may be provided to the performer to perform a specific action (i.e., a movement). In general, the viewer may provide a selection input on at least one reward from a plurality of rewards displayed for the viewer on the viewer device. Such viewer input may be tracked by the communication module 164 to determine an action (i.e., a movement) to be performed by the performer. In at least some embodiments, the viewer may have to make payment corresponding to the reward selected by the viewer which is explained in further detail later.

The communication module 164 is configured to forward the motion data and the viewer input to the virtual performance simulation module 158. The virtual performance simulation module 158 in conjunction with the instructions in the memory 154 is configured to simulate the virtual performance corresponding to the physical performance of the performer which is explained in detail next with reference to FIG. 3.

FIG. 3 is a block diagram of the virtual performance simulation module 158 for illustrating a processing of motion data 302 to generate a virtual performance 324 for content viewers, in accordance with an embodiment of the invention. As explained with reference to FIG. 2, the communication module 164 may receive motion data corresponding to movements of the performer and viewer inputs (i.e., selection of a reward correspond to an action) and forward the received information to the processor 152 (shown in FIG. 2). Further, the virtual performance simulation module 158 is configured to receive these inputs. Accordingly, in FIG. 3, the virtual performance simulation module 158 is depicted to receive the motion data 302 and the viewer input 304 as inputs.

The virtual performance simulation module 158 is depicted to include an analysis module 306, a modeling module 308, an animation module 310, and a mixer 312. The analysis module 306 is configured to receive the motion data 302 from the motion sensors and/or the image sensors. In at least one example embodiment, the motion data 302 may correspond to movements performed by the performer in response to a viewer input from a viewer. In other words, the viewer input indicates a specific action to be performed by the performer for a reward as explained in further detail later.

The analysis module 306 of the processor 152 in conjunction with the instructions stored in the memory 154 may be configured to analyze the motion data 302 received from the motion sensors and/or the image sensor to determine movements of the performer 102. In one embodiment, the motion sensors alone are enabled to capture the motion data 302 related to the performer 102. As already explained with reference to FIG. 1, the performance of the performer 102 may be captured by the motion sensors worn by the performer 102 such as, movement of the waist may be captured by the motion sensor 104e as motion data. In another embodiment, the performance of the performer may be recorded by the image sensor and further processed to determine the motion data 302. For example, when the motion sensors do not capture performances of the performer, such as, due to electrical failure in motion sensors, the image sensor may capture the motion data 302 and provide for further processing to the system 150. In yet another embodiment, the motion data 302 from both sensors (i.e., image sensors and motion sensors) may be collated to determine movements of the performer 102. For example, facial expressions of the performer during the performance that may not be captured by the motion sensors but may be captured by the image sensor and processed by the analysis module 306 to determine movements of the performer 102, so as to render a realistic virtual performance for the viewer 110. To that effect, the analysis module 306 may include a learning algorithm trained to analyze the motion data 302 received from the motion sensors and the image sensor to interpret movements of the performer 102.

The modeling module 308 is configured to generate a virtual character corresponding to the performer. In an example embodiment, images of the performer may be captured during the live performance and the modeling module 308 may simulate the virtual character corresponding to the captured image of the performer. In another example embodiment, virtual characters corresponding to each performer may be stored in a model repository 314, and the modeling module 308 may retrieve the virtual character corresponding to the performer on receiving an information of the performer associated with the live performance. In one illustrative example, the model repository 314 may include a plurality of performer profiles associated with performers. Each performer profile may be associated with a virtual character that may be retrieved on receiving profile information, for example, a name or profile ID of the performer. Further, the virtual character may be customized based on performer preferences. In at least one example embodiment, one or more features of the virtual character may be modified based on the performer preferences. Accordingly, the performer may be presented with one or more UIs to modify some features of the virtual character. In one illustrative example, the performer may choose to modify hair style from straight hair to curly hair to change external appearance of the virtual character to make it more appealing. In another example embodiment, the viewer may also provide viewer preference for modeling the virtual character. For example, the viewer may be presented with one or more options to customize the virtual character such as, facial features, hair color, hair length, skin tone, clothes, and the like of the virtual character. It shall be noted that the feature repository 316 is configured to store a large variety of customization options for features associated with the virtual character. Some examples of features that may be modified include, but not limited to, hair style, skin tone, eye color, body structure, clothes, and accessories. The modeling module 308 forwards the virtual character to the animation module 310.

The animation module 310 in conjunction with contents of the animation repository 318 is configured to process the motion data 302 to animate the movements of the virtual character In one embodiment, the animation module 310 is configured to fetch animation movements corresponding to interpreted movements of the performer from the motion data 302 (i.e., motion data received from the motion sensors) from the animation repository 318. In one illustrative example, the performer 102 may perform a sensual move and the analysis module 306 interprets the movements which is used to fetch corresponding animated movements from the animation repository 318. In another embodiment, the motion data is translated to animated movements of the performer. More specifically, the animation module 306 maps the motion data 302 to a bone position axial data of the virtual character for animating the movements of the virtual character. In general, every movement performed by the performer is translated into a motion performed by the virtual character. It shall be noted that the animation module 310 performs real-time animation of the movements of the virtual character to render the virtual character in near real-time to the viewers.

The mixer 312 receives the animated movements of the virtual character. In addition, the mixer 312 is also configured to receive a corresponding viewer input 304 provided by the viewer i.e., the reward selected by the viewer that initiated the performer to perform specific movements. In at least one embodiment, the mixer 312 is configured to use the animated movements of the virtual character and the viewer input to select one or more special effects from a special effect repository 320 of the storage module 166.

The term 'special effect' as used herein may refer to any kind of background effects, mechanized props or audio effects that enrich and/or enhance the virtual performance of the virtual character. In one illustrative example, the viewer input 304 may correspond to a reward of $20 for performing a body roll. The performer on receiving the viewer input may perform the action (i.e., the body roll) that is captured as the motion data 302. Accordingly, the mixer 312 may select a sensual music or audio clip from the special effect repository 320 to enrich the virtual performance of the virtual character. In another illustrative example, the viewer input 304 may correspond to a sensual dance move that may show the animated character performing moves with a chair (for example, resting hands on a chair), the mixer 312 may automatically select a stylistic chair (i.e., a mechanized prop) from the special effect repository 320.

In at least one embodiment, the term 'special effect' as used herein may refer to a count-down timer. The application may cause display of a count-down timer on the viewer display 1012 for perusal of the viewer, specially, upon detecting receiving of the tip from the viewer. A time period of the count-down timer is determined which is directly proportional to amount of the tip sent by the viewer and is equivalent to the time period of vibration of the adult toy used by the performer. In other words, a control signal instructs the controller to actuate the vibration motor of the adult toy for the time period of the count-down timer. For instance, if the adult toy is going to vibrate for 10 seconds, the application may generate sequential labels for the count-down time as 10, 9, 8, 7, 6, 5, 4, 3, 2, 1. It may be appreciated that the special effect (e.g., the countdown timer) let the viewer be familiar with the status of the adult toy. Further, the application is also configured to display a confirmation for perusal of the user upon receiving of the tip by the at least one viewer on the user display. It is contemplated that the received tip amounts are credited to the user's (model's) account and made redeemable by the respective user at a later time.

In at least one embodiment, the term 'special effect' as used herein may refer to a control pattern indicating the real time strength, pattern, and other status information of the adult toy. For example, the control pattern may include at least one instruction signal set that may actuate adult toy to sequentially perform one or more series of different pre-defined acts and/or different levels of the one or more predefined acts, wherein a given type or kind of predefined act or a given level of the predefined act may correspond to a given instruction signal. Different instruction signals together may comprise an instruction signal set. The instruction signals may be configured to cause customization of the predefined act such as, for example, vibration, rotation, swinging, inhalation, temperature variation, expansion, suction, and contraction of the adult toy. Different levels of the predefined act may include amplitude, frequency, acceleration, temperature, periodicity, and/or duration.

In at least one embodiment, the term 'special effect' as used herein may refer to a Logo Text Effect associated with the adult toy. The Logo Text Effect shows the text in different effects and is configured to indicate the real time strength, control pattern, and other status information of the adult toy. For example, the Logo Text associated with the adult toy may gradually become larger as the vibration strength of the adult toy increases, and gradually become smaller as the vibration strength of the adult toy decrease. Alternatively, the Logo Text associated with the adult toy may beat faster as the frequency of the expansion and contraction of the adult toy increases, and beat slower as the frequency of the expansion and contraction of the adult toy decreases. The Logo Text associated with the adult toy may be the product name or brand of the adult toy.

In addition to receiving the motion data corresponding to the performer, the communication module 164 may also receive status data related to the adult toy used by a performer. The status data related to the adult toy comprises motion data detected by sensors coupled to the adult toy. For example, a accelerometer coupled to the adult toy may detect displacement speed, shaking speed, and direction data of the adult toy, and a pressure sensor coupled to the adult toy can detect pressure data acting on the adult toy, and a temperature sensor coupled to the adult toy can detect temperature data of the adult toy, etc. The status data related to the adult toy comprises control signal for actuating adult toy to sequentially perform one or more series of different predefined acts and/or different levels of the one or more predefined acts.

In at least one embodiment, the mixer 312 is capable of performing video mixing to generate the virtual performance 324. More specifically, the animated movements of the virtual character are combined/blended with the special effects to generate the virtual performance 324. In video mixing, multiple video signals, images and/or audio signals are adjusted and combined (or blended) into a single video signal. For example, during video mixing, background effects and props are super imposed on a video signal comprising the animated movements of the virtual character. During video mixing, one or more video parameters (i.e., volume level, frequency, timing information of movements, etc.) of the video signals are manipulated or enhanced to generate the single video (i.e., the virtual performance 324). The virtual performance 324 is a simulation of the physical performance corresponding to the performer and provides an enhanced experience of for the viewers of the virtual performance 324.

Referring now to FIG. 2, the virtual performance 324 corresponding to the physical performance of the performer may be forwarded to the communication module 162. The communication module 162 is configured to facilitate broadcast of the virtual performance such as the virtual performance 324 to electronic devices associated with one or more content viewers such as, viewer device 112 associated with the viewer 110. Such an enriched virtual performance provides an enhanced feeling, and thereby simulates a sensual experience for viewers of the virtual performance 324. An example of such virtual performance with a virtual character livestreamed on a viewer device is shown and explained with reference to FIG. 4.

In some example embodiments, the communication module 162 may also receive performer inputs from a performer device associated with the performer, for example, the performer device 106 associated with the performer 102. The communication module 162 forwards the performer inputs to the reward management module 158 of the processor 152. The performer inputs include information related to an action and a corresponding reward. More specifically, action corresponds to a movement to be performed by the performer and the reward corresponds to a tip information or payment. In general, the viewer pays and requests the performer to perform a specific action that may be translated to motion of the virtual character.

The reward management module 158 manages these performer inputs and accordingly, the reward management module 158 facilitates display of such performer inputs as selectable options on a UI of the viewer device. For example, selectable options for a dance performance may include options such as, roll over, crawl, body roll, hip dips, reveal, take off clothes, and the like. In addition, the reward management module 158 is also configured to receive viewer inputs on selectable options from the viewer. For example, the viewer may provide a touch/click input on a selectable option displayed on the viewer device and such viewer input (i.e., the selected reward) is sent to the system 150 for further processing as will be explained in further detail later. An example of such selectable options displayed on a UI of a viewer device is explained next with reference to FIG. 4.

Figure 4:
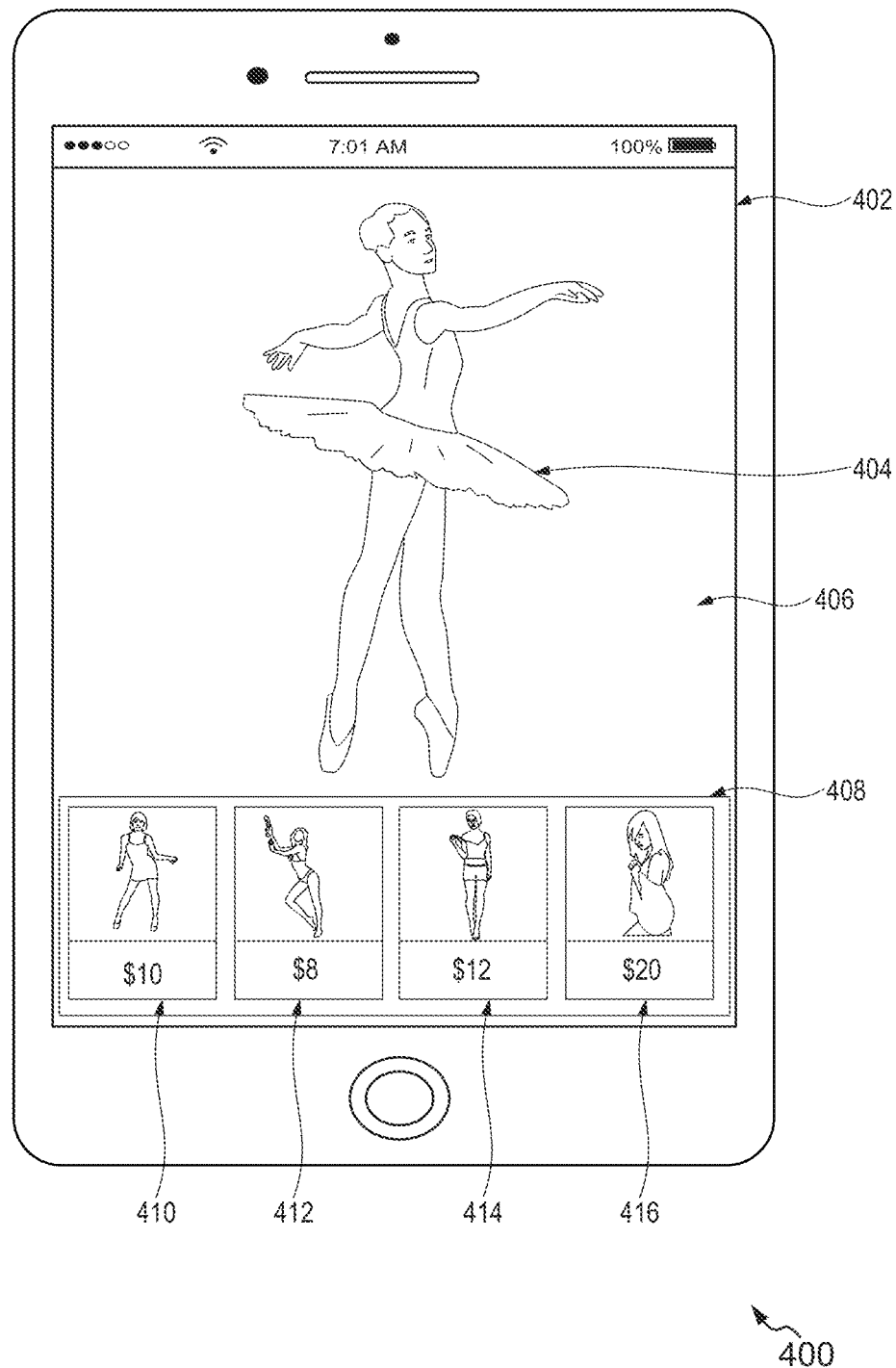
FIG. 4 shows a viewer device displaying an UI of a virtual performance simulating a physical performance of a performer, in accordance with an embodiment of the invention.

FIG. 4 shows the viewer device 400 displaying an UI 402 of a virtual performance 406 simulating a physical performance of a performer, in accordance with an embodiment of the invention. As explained with reference to FIG. 3, the virtual performance 406 is generated by animating movements of a virtual character 404. The movements of the virtual character 404 are animated based at least on motion data captured by motion sensors worn on body of the performer such as, the performer 102. The virtual performance 406 is enriched with special effects to provide an enhanced experience for viewers of the virtual performance 406. Accordingly, the UI 402 displays a video associated with the virtual performance 406 in which movements of the virtual character 404 mimic the performance of the performer performing at a venue. It shall be noted that although the UI 402 depicts the viewer using a mobile application to view the virtual performance, a web browser application may be used to access a website that broadcasts virtual performances from a remote web server (e.g., the digital platform server 135) over a network such as, the network 140.

An application (not shown in FIG. 4) associated with a livestreaming service provider (for example, the digital platform server 135 shown in FIG. 1) installed in the viewer device 400 facilitates broadcasting of the virtual performance of the virtual character 404. Accordingly, the content provider may facilitate display of the UI 402 configured to provide selectable options to the viewers (not shown in FIG. 4) of the virtual performance 406 to interact with the performer (not shown in FIG. 4). To this effect, the application may cause display of a widget 408 including several selectable options for the content viewer (e.g., the viewer 110) to request the performer to perform a specific action. In one embodiment, these selectable options may correspond to performer inputs received from the performer acting or staging a performance that is broadcasted as the virtual performance 406. Alternatively, the UI 402 may include some default selectable options that may be displayed based on the performance being broadcasted by the system 150 facilitating broadcast of the virtual performance 406.

The widget 408 is depicted to include a plurality of selectable options for the content viewer. In some embodiments, the widget 408 may be a dynamic widget, wherein the options displayed on the widget 408 may change or adapt based on the performer inputs during the performance. Alternatively, in some embodiments, the widget 408 may be a floating widget, which may appear only when the performer completes a set of moves/actions and prepares to perform the next set of movements during the physical performance.

As an example, the content viewer is depicted to have been provided with a plurality of selectable icons 410, 412, 414 and 416 on the widget 408. The plurality of selectable icons 410, 412, 414 and 416 are depicted to display a reward information along with respective actions to be performed by the performer. For example, the selectable icon 410 represents a $10 for body roll move, the selectable icon 412 represents $8 for performing using an adult toy 1, the selectable icon 414 represents $12 for a strip tease and the selectable icon 416 represents a $20 for a reveal. In one illustrative example, the viewer can click on the selectable icon 410, if he/she wants the performer to perform a body roll move. In another illustrative example, the viewer may want to view the virtual performance 406 of the virtual character 404 mimicking the performer when he/she performs with an adult toy, such as the adult toy 108 (e.g., a dildo). Accordingly, the viewer may provide a touch/click input on the selectable icon 412. On providing a viewer input on a selectable option, the viewer may be presented with one or more UIs to make a payment. More specifically, the viewer has to pay the specified amount (i.e., shown as reward) to request the performer to perform a specific move. The payment may be processed between the viewer and the performer via digital payment methods known in the art.

It is noted that the icons/options displayed on the widget 408 of the UI 402 are shown herein for illustration purposes. In some embodiments, the options/icons displayed on the widget 408 may be performance-specific (i.e., related to the performance) or specific to the performer. For example, the UI 402 may display different icons or options related to actions previously performed by the performer during prior sessions (i.e., actions performed in prior physical performances). Similarly, for a physical performance, such as a musical concert or dance performance, the widget 408 may include a different set of icons and options for the viewer to request the performer to perform a specific action/movement. Further, the use of selectable options may be replaced with voice input and gesture input as forms for providing viewer inputs. Moreover, other forms of expressions, such as text messaging options, selectable Graphics Interchange Format (GIFs), video uploading options, etc., which are capable of enabling the content viewer to express his or her expected action by the performer may also be provided on the widget 408 to enhance a viewing experience of the content viewer.

Referring back to FIG. 2, such viewer input on a selectable icon is received by the communication module 162 of the system 150. The communication module 162 forwards the viewer input to the reward management module 158. The reward management module 158 is configured to determine if the requested action is to be performed by the performer or if the reward corresponds to a request for performance with an adult toy, such as, the adult toy 108. If the reward corresponds to an action to be performed by a performer, the reward management module 158 generates a notification including the action for the viewer. In one illustrative example, if the viewer had provided a viewer input on the selectable icon 414, the reward management module 158 determines that the action (i.e., strip tease) has to be performed by the performer and accordingly, generates a notification including the reward and the action (i.e., strip tease) to be performed. Alternatively, when the viewer input indicates that the performer has to perform using an adult toy, then the reward management module 158 performs a look up in the control pattern repository 322 (shown in FIG. 3) of the storage module 164 to determine a control pattern corresponding to the viewer input. In one illustrative example, when the viewer selects the option 412 corresponding to an action where the performer has to perform with an adult toy, then the reward management module 158 identifies a control pattern to operate the adult toy based on the viewer input. In at least one example embodiment, the reward management module 158 generates a notification comprising the control pattern. The notification is forwarded to the communication module 162. The communication module 162 transmits the notification to the performer device, for example, the performer device 106.

In one embodiment, the performer may alter his/her action (i.e., movements) based on the notification. For example, when the notification indicates a reward for performing a strip tease, the performer may alter his/her movements to perform the strip tease. In another embodiment, the performer device on receiving the notification including the control pattern activates a corresponding adult toy. More specifically, the performer device sends the control pattern to operate the adult toy and the performer performs with the adult toy. It shall be noted that the performer may be associated with a plurality of adult toys and the viewer input may correspond to performing with a specific adult toy and as such, the performer device connects with the specific adult toy and controls operation of the adult toy based on the control pattern. As such, the motion sensors on the body of the performer may capture the motion data as explained earlier and transfer the motion data to the system 150. The system 150 processes the motion data to animate movements of the virtual character as explained with reference to FIG. 3.

Figure 5:
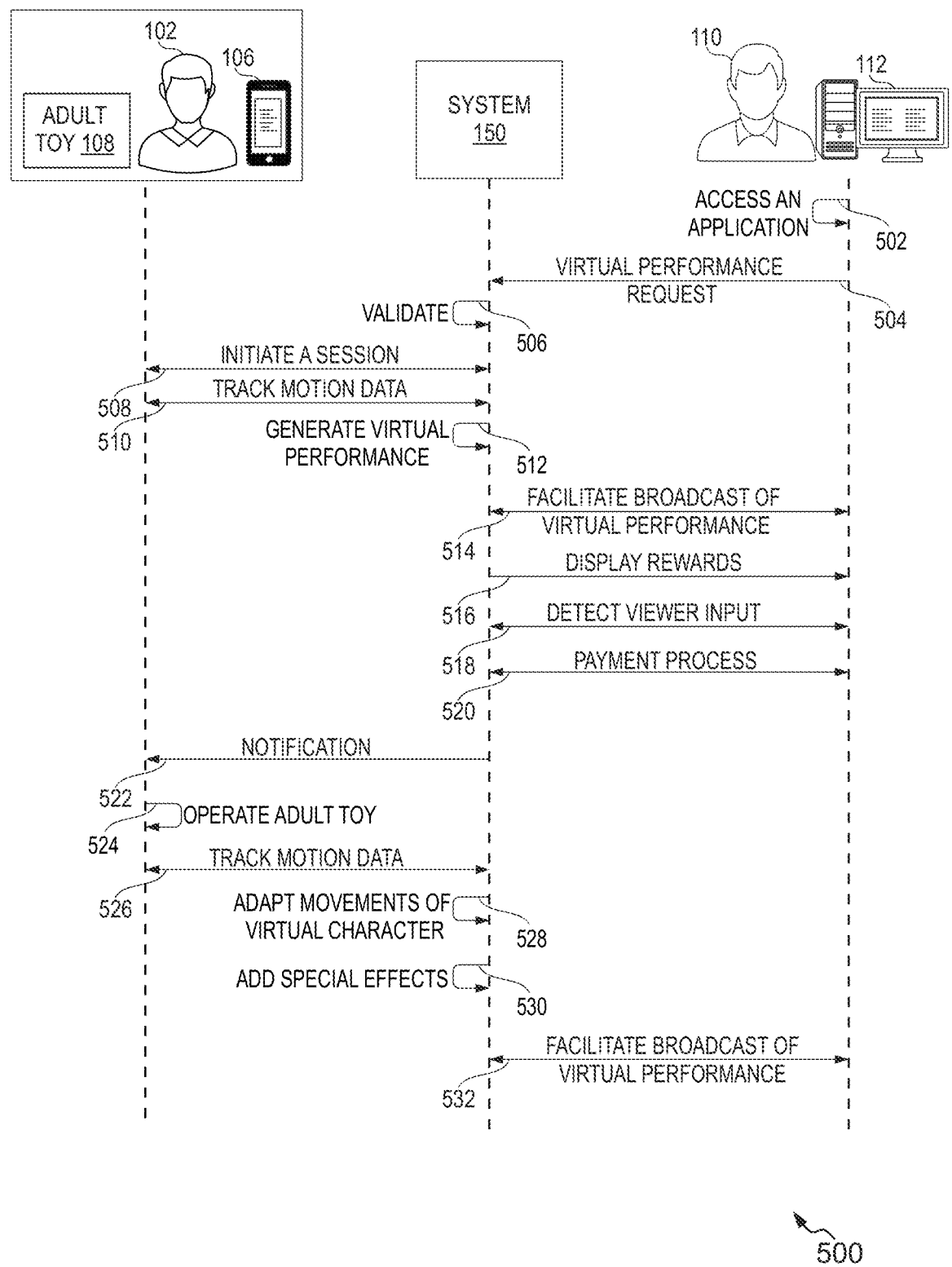
FIG. 5 is a sequence flow diagram for illustrating a process flow for broadcasting a virtual performance for content viewers, in accordance with an embodiment of the invention.

FIG. 5 is a sequence flow diagram 500 for illustrating a process flow for simulating a virtual performance using a virtual character for a viewer 110, in accordance with an embodiment of the invention. The process flow 500 starts at 502.

At 502, the viewer accesses a UI of a mobile/web application associated with a livestreaming service provider such as, the digital platform server 135 (shown in FIG. 1) for viewing a virtual performance.

At 504, the system 150 receives a virtual performance request from the viewer. In general, the viewer may provide a preference for viewing select virtual performance on the viewer device 112. In one illustrative example, the viewer may select a category of performance and/or name of a performer desired by the viewer.

At 506, the system 150 validates the virtual performance request of the viewer 110. More specifically, the system performs a check to determine a performer for example, the performer 102.

At 508, the system 150 initiates a session with the performer 102. The performer is notified and the performer starts performing for the viewer.

At 510, the system 150 tracks motion data associated with physical performance of the performer 102. In one embodiment, the motion data may be captured by motion sensors worn on specific parts of a body of a performer such as, the performer 102. More specifically, the motion sensors are enclosed in a piece of cloth and wrapped around specific parts of the performer's body, for instance, hands, shoulders, trunk, waist, feet, neck and head. During a physical performance, when the performer moves about, for example, dances to a tune, force, angular velocity and orientation of each of the motion sensors are captured to determine the motion data. In another embodiment, the motion data may be received from an image sensor capturing performance of the performer 102. It shall be noted that more than one image sensor may be deployed to capture the performance of the performer and as such, the image sensors may be installed at different location of an enclosed space such as, an event venue. In yet another example embodiment, the motion data from the motion sensors and the image sensors are collated together to determine movements of the performer 102.

At 512, the system 150 generates a virtual performance corresponding to the physical performance of the performer. More specifically, a virtual character corresponding to the performer is generated and movements of the virtual character are animated based on the motion data.

At 514, the system 150 facilitates broadcast of the virtual performance in real-time to the viewer device 112.

At 516, the system 150 facilitates display of selectable options on the UI for the viewer on the viewer device 112. The selectable options correspond to different rewards for the performer. More specifically, each reward is associated with an action to be performed by the performer. In one illustrative example, if the virtual performance is a virtual dance show, the selectable options may correspond to different reward information, for example, $2, $5, $10, $20, etc. Each of these rewards may be associated with different genres of music, for example, folk music, pop music, disco music, electronic dance music and the like.

At 518, the system 150 detects a viewer input on a selectable option. In one illustrative example, if the viewer wants the performer to perform for disco music, the viewer may select a reward of $10 associated with the disco music.

At 520, the system 150 may facilitate processing of payment based on the viewer input. When the viewer provides a viewer input on a reward (i.e., a selectable option), a payment page may be presented to the viewer for processing payment from the viewer to the performer. Some examples of payments include, but not limited to, payment cards (e.g., debit cards, credit cards, prepaid cards, virtual payment numbers, digital wallet cards, virtual card numbers, forex cards, charge cards and stored-value cards), internet banking, digital wallets, mobile banking, digital payment apps and the like.

At 522, the system 150 sends a notification to a performer device 106 associated with the performer 102. In one example embodiment, the notification may indicate the viewer input and corresponding action to be performed by the performer. In one illustrative example, if the viewer had selected a reward corresponding to the disco dance, the performer receives notification of the reward and corresponding action (i.e., change dance moves to disco dance). The performer on receiving the notification may perform the action (i.e., disco dance) for the viewer. In another embodiment, the notification may include a control pattern to operate at least one adult toy, for example, the adult toy 108 (shown in FIG. 1).

At 524, the performer device 106 may operate the adult toy 108 to provide a physical stimulus to the performer 102. Accordingly, the adult toy 108 may be equipped with wireless communication capabilities to receive the control pattern from the performer device 106.

At 526, the system 150 tracks the motion data of the performer in response to the viewer input. As already explained, the motion sensors capture motion data corresponding to movements of the performer 102 and transmit it to the system 150.

At 528, movements of the virtual character may be adapted based on the motion data.

At 530, the system 150 may add one or more special effects to enhance the virtual performance of the virtual character. For example, the system 150 may append sound effects, background effects or mechanized props to enhance the virtual performance.

At 532, the system 150 facilitates broadcasting of the virtual performance to content viewers such as, the viewer 110. The process flow 500 ends at 532.

A method for simulating a virtual performance with a virtual character corresponding to a live performance of the performer for viewers is explained with reference to FIG. 6.

Figure 6:
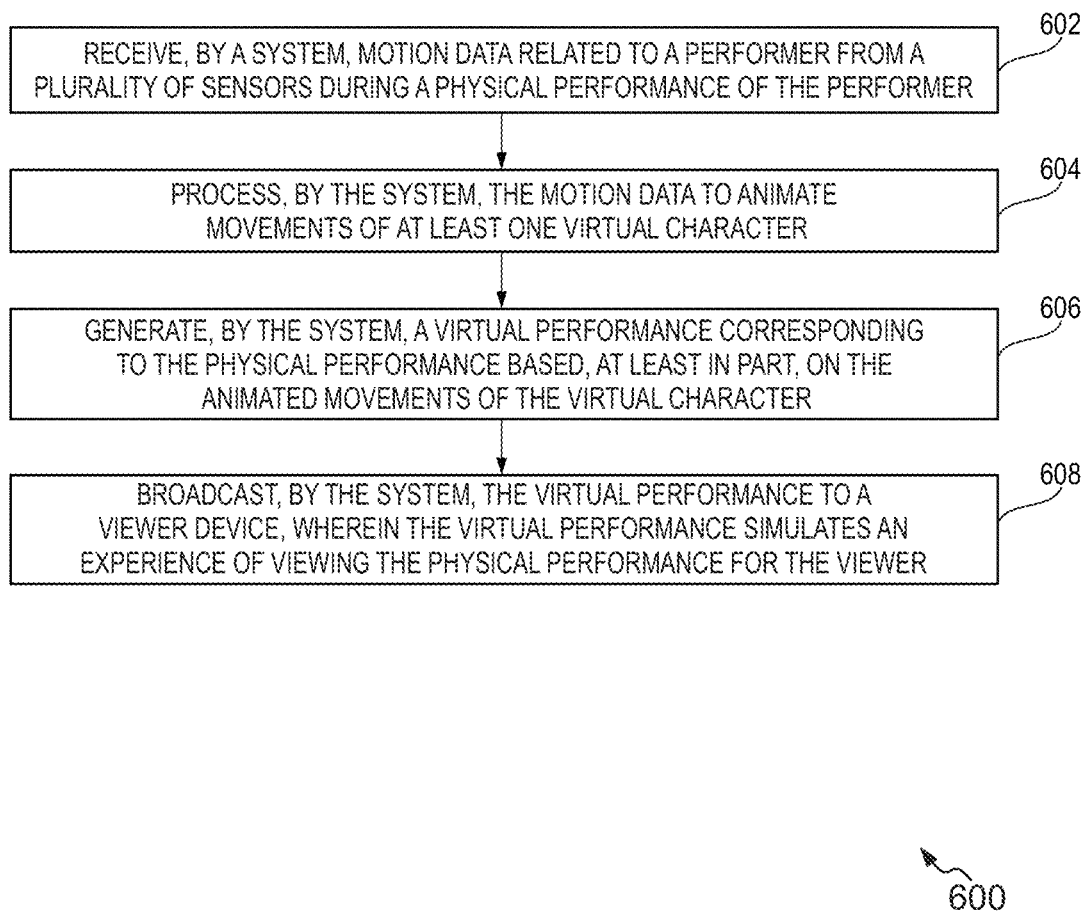
FIG. 6 shows a flow diagram of a computer-implemented method for broadcasting virtual performance, in accordance with an embodiment of the invention.

FIG. 6 shows a flow diagram of a method 600 for broadcasting a virtual performance that simulates a physical performance, in accordance with an embodiment of the invention. The various steps and/or operations of the flow diagram, and combinations of steps/operations in the flow diagram, may be implemented by, for example, hardware, firmware, a processor, circuitry and/or by a system such as the system 150 explained with reference to FIGS. 1 to 5 and/or by a different device associated with the execution of software that includes one or more computer program instructions. The method 600 starts at operation 602.

At operation 602 of the method 600, motion data related to a performer is received by a system such as, the system 150 explained with reference to FIGS. 1 to 5 from plurality of sensors during a physical performance of the performer. In at least one example embodiment, the plurality of sensors correspond to one or more of: motion sensors and image sensors. Each motion sensor may be configured on a different location on a body of the performer. For example, the motion sensors are enclosed in a material such as, a piece of cloth. The said cloth is wrapped around specific parts of the performer's body, for instance, hands, shoulders, waist, feet and head. The image sensor may be installed/positioned in an enclosed space, such as, the event venue where the performer is performing. The image sensor is configured to capture video signal (i.e., a plurality of image frames) when a performer is staging an act. It shall be noted that more than one performer may perform in the physical performance and accordingly, the motion data of all the performers are received by the system for further processing.

At operation 604 of the method 600, the motion data is processed to animate movements of at least one virtual character. The virtual character corresponding to a performer may be retrieved from a model repository (see, model repository 314 of FIG. 3). In some example embodiments, the performer is provided with options to customize the virtual character. More specifically, the performer can modify one or more features of the virtual character on a performer device associated with the performer. In one illustrative example, the body structure of the virtual character may be customized. Some examples of features of the virtual character that can be modified include, but not limited to, a hair style, a skin tone, an eye color, a body structure, a dress, and an accessory. To animate the movements of the at least one virtual character, the motion data is mapped to a bone position axial data of a virtual character. It shall be noted that although only one performer performs during the physical performance, the motion data may be used to simulate movements of the performer on two different virtual characters, for example, two different virtual characters with different features, for example, body structures may be simulated to mimic movements of the performer.

At operation 606 of the method 600, a virtual performance corresponding to the physical performance is generated based, at least in part, on the animated movements of the at least one virtual character. In some example embodiments, special effects may be synthesized based on the animated movements of the virtual character. To that effect, an appropriate special effect may be selected from a special effect repository (see, special effect repository 320 shown in FIG. 3) and mixed or blended with the virtual character. Some examples of special effects include, but not limited to, a background effect, a mechanized prop and an audio effect. In one illustrative example, animated movements of the virtual character may indicate a sensuous dance move and accordingly, the system synthesizes an audio signal based on the dance moves which is later appended with the virtual character to enhance the virtual performance.

At operation 608 of the method 600, the virtual performance is broadcasted to a viewer device for performing a playback of the virtual performance. The virtual performance simulates an experience of viewing the physical performance for the viewer. The method 600 ends at operation 608.

Figure 7:
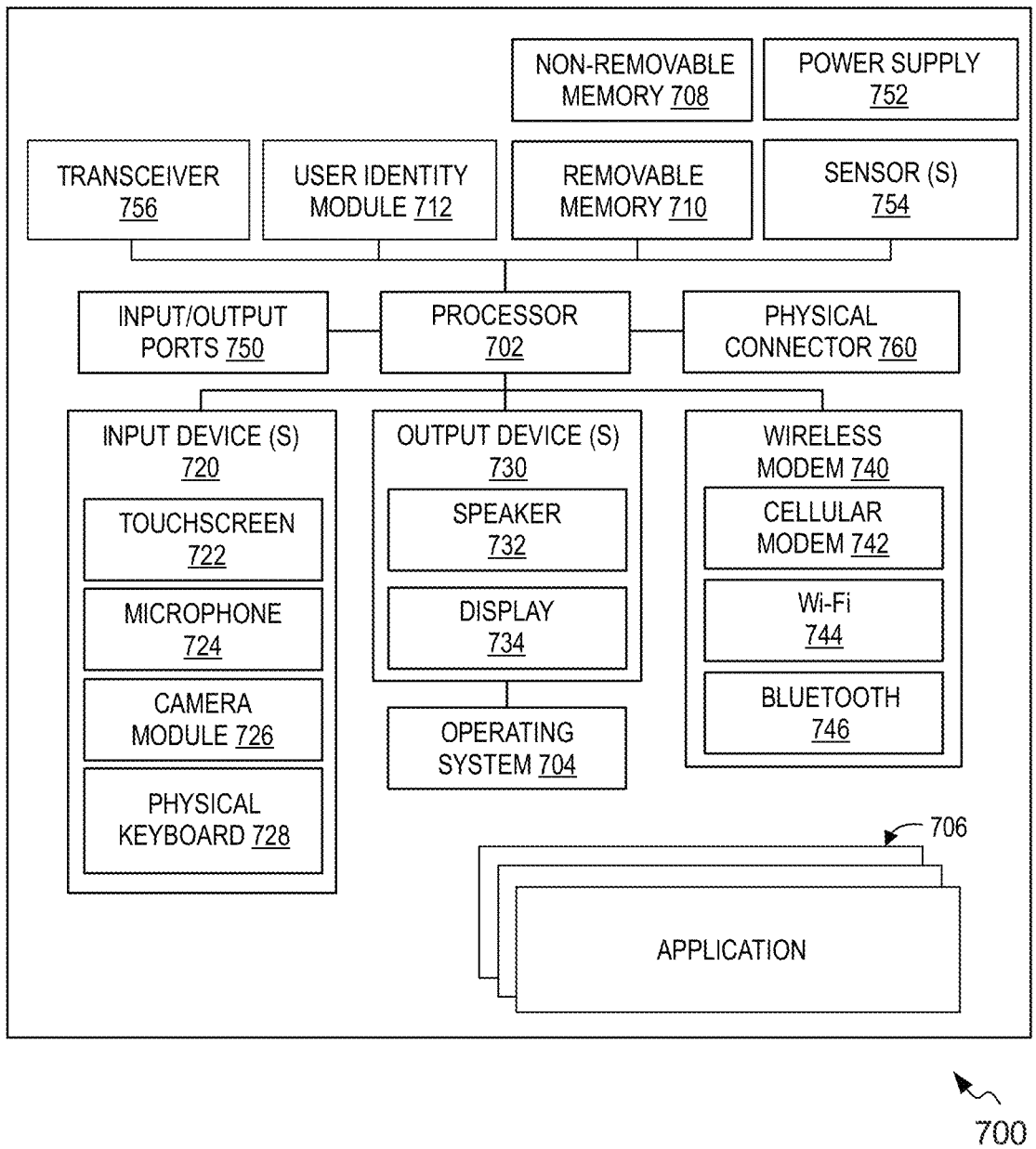
FIG. 7 is a simplified block diagram of an electronic device capable of implementing various embodiments of the present disclosure.

FIG. 7 is a simplified block diagram of an electronic device 700 capable of implementing various embodiments of the present disclosure. For example, the electronic device 700 may correspond to the performer device 106 or the viewer device 112 of FIG. 1. The electronic device 700 is depicted to include one or more applications 706. For example, the one or more applications 706 may include an application configured to facilitate broadcasting of virtual performances for viewers. One of the one or more applications 706 installed on the electronic device 700 are capable of communicating with a system such as, the system 150 for controlling performance of the performer.

It should be understood that the electronic device 700 as illustrated and hereinafter described is merely illustrative of one type of device and should not be taken to limit the scope of the embodiments. As such, it should be appreciated that at least some of the components described below in connection with the electronic device 700 may be optional and thus in an embodiment may include more, less or different components than those described in connection with the embodiment of the FIG. 7. As such, among other examples, the electronic device 700 could be any of a mobile electronic device, for example, cellular phones, tablet computers, laptops, mobile computers, personal digital assistants (PDAs), mobile televisions, mobile digital assistants, or any combination of the aforementioned, and other types of communication or multimedia devices.

The illustrated electronic device 700 includes a controller or a processor 702 (e.g., a signal processor, microprocessor, ASIC, or other control and processing logic circuitry) for performing such tasks as signal coding, data processing, image processing, input/output processing, power control, and/or other functions. An operating system 704 controls the allocation and usage of the components of the electronic device 700 and supports for one or more operations of the application (see, the applications 706), that implements one or more of the innovative features described herein. In addition, the applications 706 may include common mobile computing applications (e.g., telephony applications, email applications, calendars, contact managers, web browsers, messaging applications) or any other computing application.

The illustrated electronic device 700 includes one or more memory components, for example, a non-removable memory 708 and/or removable memory 710. The non-removable memory 708 and/or the removable memory 710 may be collectively known as a database in an embodiment. The non-removable memory 708 can include RAM, ROM, flash memory, a hard disk, or other well-known memory storage technologies. The removable memory 710 can include flash memory, smart cards, or a Subscriber Identity Module (SIM). The one or more memory components can be used for storing data and/or code for running the operating system 704 and the applications 706. The electronic device 700 may further include a user identity module (UIM) 712. The UIM 712 may be a memory device having a processor built in. The UIM 712 may include, for example, a subscriber identity module (SIM), a universal integrated circuit card (UICC), a universal subscriber identity module (USIM), a removable user identity module (R-UIM), or any other smart card. The UIM 712 typically stores information elements related to a mobile subscriber. The UIM 712 in form of the SIM card is well known in Global System for Mobile (GSM) communication systems, Code Division Multiple Access (CDMA) systems, or with third-generation (3G) wireless communication protocols such as Universal Mobile Telecommunications System (UMTS), CDMA9000, wideband CDMA (WCDMA) and time division-synchronous CDMA (TD-SCDMA), or with fourth-generation (4G) wireless communication protocols such as LTE (Long-Term Evolution).

The electronic device 700 can support one or more input devices 720 and one or more output devices 730. Examples of the input devices 720 may include, but are not limited to, a touch screen/a display screen 722 (e.g., capable of capturing finger tap inputs, finger gesture inputs, multi-finger tap inputs, multi-finger gesture inputs, or keystroke inputs from a virtual keyboard or keypad), a microphone 724 (e.g., capable of capturing voice input), a camera module 726 (e.g., capable of capturing still picture images and/or video images) and a physical keyboard 728. Examples of the output devices 730 may include, but are not limited to, a speaker 732 and a display 734. Other possible output devices can include piezoelectric or other haptic output devices. Some devices can serve more than one input/output function. For example, the touch screen 722 and the display 734 can be combined into a single input/output device.

A wireless modem 740 can be coupled to one or more antennas (not shown in FIG. 7) and can support two-way communications between the processor 702 and external devices, as is well understood in the art. The wireless modem 740 is shown generically and can include, for example, a cellular modem 742 for communicating at long range with the mobile communication network, a Wi-Fi compatible modem 744 for communicating at short range with an external Bluetooth-equipped device or a local wireless data network or router, and/or a Bluetooth-compatible modem 746. The wireless modem 740 is typically configured for communication with one or more cellular networks, such as a GSM network for data and voice communications within a single cellular network, between cellular networks, or between the electronic device 700 and a public switched telephone network (PSTN).

The electronic device 700 can further include one or more input/output ports 750, a power supply 752, one or more sensors 754 for example, an accelerometer, a gyroscope, a compass, or an infrared proximity sensor for detecting the orientation or motion of the electronic device 700 and biometric sensors for scanning biometric identity of an authorized user, a transceiver 756 (for wirelessly transmitting analog or digital signals) and/or a physical connector 760, which can be a USB port, IEEE 1294 (FireWire) port, and/or RS-232 port. The illustrated components are not required or all-inclusive, as any of the components shown can be deleted and other components can be added.

Various embodiments disclosed herein provide numerous advantages. More specifically, the embodiments disclosed herein suggest techniques for simulating a virtual performance that mimics a physical performance of a performer. The movements of the performer are animated to render enhanced virtual performance for the viewers in real-time. Moreover, the addition of special effects creates an enriched virtual performance for the content viewers. Some parameters of special effects are expertly adapted to mix with animated movements of the virtual character. The viewers of the virtual performance, i.e., the content viewers, are provided with several selectable options to request a specific movement/action from the performer. As the content viewer is engaged throughout the virtual performance (by sharing viewer inputs), the virtual performance provides an interactive platform where an overall experience of the viewer of the virtual performance is increased manifold.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

What is claimed is:

1. A computer-implemented method for broadcasting virtual performance, the method comprising:
- receiving, by a system, status data related to an adult toy used by a performer;
- processing, by the system, the status data to animate performance of a virtual object associated with the adult toy;
- generating, by the system, virtual performance of the virtual object based, at least in part, on the animated performance of the virtual object;
- broadcasting, by the system, the virtual performance to a viewer device, wherein the virtual performance includes the virtual performance of the virtual object corresponding to the performance of the adult toy that is used by the performer; and
- causing, by the system, display of the virtual performance of the virtual object on the viewer device.

2. The method as claimed in claim 1, wherein the status data is related to sensors coupled to the adult toy.

3. The method as claimed in claim 1, wherein the status data is related to a control signal of the adult toy, wherein the control signal is used for controlling the adult toy to perform a predefined action.

4. The method as claimed in claim 3, wherein the virtual performance of the virtual object and the performance of the adult toy are synchronized or near synchronized in real-time and corresponding to the control signal of the adult toy.

5. The method as claimed in claim 3, wherein the status data is related to rewards from the viewer, and each reward is associated with at least one control signal of the adult toy.

6. The method as claimed in claim 1, wherein the virtual performance of the virtual object includes at least one of image, video or special effects corresponding to the status data related to the adult toy.

7. The method as claimed in claim 6, wherein at least one of the image, video or special effects is characterized by at least one of a count-down timer, a control pattern and a Logo Text Effect associated with the adult toy corresponding to the status data related to the adult toy.

8. The method as claimed in claim 1, further comprising:
- receiving, by a system, motion data related to a performer during a physical performance of the performer;
- processing, by the system, the motion data to animate movements of at least one virtual character;
- generating, by the system, virtual performance corresponding to the physical performance based, at least in part, on the animated motion of the at least one virtual character;
- broadcasting, by the system, the virtual performance to a viewer device, wherein the virtual performance simulates an experience of viewing the physical performance of the performer for the viewer;
- causing, by the system, display of the virtual performance of the at least one virtual character and at least one virtual adult toy on the viewer device.

9. The method as claimed in claim 8, wherein the motion data is related to a plurality of sensors associated with the performer, wherein one or more sensors of the plurality of sensors includes at least one of action sensors worn by the performer and image sensors to capture the status data of the performer.

10. A system, comprising:
- a non-volatile memory, which comprises computer-executable code stored in the non-volatile memory;
- a processor;
- wherein, the computer-executable code, when operating on the processor, causes the system to:
- receive status data related to an adult toy used by a performer;
- process the status data to animate performance of a virtual object associated with the adult toy;
- generate virtual performance of the virtual object based, at least in part, on the animated performance of the virtual object;
- broadcast the virtual performance to a viewer device, wherein the virtual performance includes the virtual performance of the virtual object corresponding to the performance of the adult toy that is used by the performer; and
- cause display of the virtual performance of the virtual object on the viewer device.

11. The system as claimed in claim 10, wherein the status data is related to sensors coupled to the adult toy.

12. The system as claimed in claim 10, wherein the status data is related to a control signal of the adult toy, wherein the control signal is used for controlling the adult toy to perform a predefined action.

13. The system as claimed in claim 12, wherein the virtual performance of the virtual object and the performance of the adult toy are synchronized or near synchronized in real-time and corresponding to the control signal of the adult toy.

14. The system as claimed in claim 12, wherein the status data is related to rewards from the viewer, and each reward is associated with at least one control signal of the adult toy.

15. The system as claimed in claim 10, wherein the virtual performance of the virtual object includes at least one of video or special effects corresponding to the status data related to the adult toy.

16. The system as claimed in claim 10, wherein, the computer-executable code, when operating on the processor, further causes the system to:
- receive motion data related to a performer during a physical performance of the performer;
- process the motion data to animate movements of at least one virtual character;
- generate virtual performance corresponding to the physical performance based, at least in part, on the animated motion of the at least one virtual character;
- broadcast the virtual performance to a viewer device, wherein the virtual performance simulates an experience of viewing the physical performance of the performer for the viewer;
- cause display of the virtual performance of the at least one virtual character and at least one virtual adult toy on the viewer device.

17. The system as claimed in claim 16, wherein the motion data is related to a plurality of sensors associated with the performer.

18. The system as claimed in claim 17, wherein one or more sensors of the plurality of sensors includes at least one of action sensors worn by the performer and image sensors to capture the status data of the performer.

19. A non-transitory computer-readable storage medium, comprising:
machine-readable instructions,
the machine-readable instructions when executed by a processor of a controller, enable the controller to:
receive status data related to an adult toy used by a performer during a physical performance of the performer;
process the status data to animate performance of a virtual object associated with the adult toy;
generate virtual performance of the virtual object based, at least in part, on the animated performance of the virtual object;
broadcast the virtual performance to a viewer device, wherein the virtual performance includes the virtual performance of the virtual object corresponding to the performance of the adult toy that is used by the performer; and
cause display of the virtual performance of the virtual object on the viewer device.

20. The non-transitory computer-readable storage medium as claimed in claim 19, wherein the virtual performance of the virtual object includes at least one of video or special effects corresponding to the status data related to an adult toy.

* * * * *